United States Patent [19]

Schmidt-Radde et al.

[11] Patent Number: 5,710,284
[45] Date of Patent: Jan. 20, 1998

[54] PURIFICATION OF N-VINYLPYRROLIDONE BY CRYSTALLIZATION

[75] Inventors: Martin Schmidt-Radde, Beindersheim; Herbert Helfert, Frankenthal; Bernd Eck, Viernheim; Bernhard Maltry, Obrigheim, all of Germany

[73] Assignee: BASF Aktiengesellschaft, Ludwigshafen, Germany

[21] Appl. No.: 708,820

[22] Filed: Sep. 9, 1996

[30] Foreign Application Priority Data

Oct. 2, 1995 [DE] Germany .............. 195 36 859.2

[51] Int. Cl.⁶ .................................. C07D 207/08
[52] U.S. Cl. .......................... 548/543; 548/555
[58] Field of Search ................... 548/543, 555

[56] References Cited

U.S. PATENT DOCUMENTS

| | | | |
|---|---|---|---|
| 3,597,164 | 8/1971 | Ab-Der-Halden et al. | 23/273 F |
| 4,873,336 | 10/1989 | Liu et al. | 546/243 |
| 5,039,817 | 8/1991 | Kroker et al. | 548/543 |
| 5,329,021 | 7/1994 | Cohen et al. | 548/543 |

*Primary Examiner*—Joseph K. McKane
*Attorney, Agent, or Firm*—Keil & Weinkauf

[57] ABSTRACT

In a process for purifying N-vinylpyrrolidone by crystallization in a crystallizer, those surfaces of the crystallizer from which crystals grow during the crystallization are covered with an N-vinylpyrrolidone seed layer before the crystallization.

8 Claims, 2 Drawing Sheets

PURIFICATION OF N-VINYLPYRROLIDONE BY CRYSTALLIZATION

The present invention relates to a process for purifying N-vinylpyrrolidone by crystallization.

Polymerized vinylpyrrolidone is widely used for cosmetic products, in the drugs sector or in the foodstuff industry.

In the preparation of N-vinylpyrrolidone by vinylation of pyrrolidone with acetylene, the product obtained after the synthesis and distillation contains 1 to 10% by weight of pyrrolidone plus nitrogen and vinyl ether compounds in the ppm range as impurities. For the applications mentioned above, >0.1% by weight of total impurities in the product is not tolerated. In addition, some nitrogen compounds may lead to unacceptable discoloration of products and problems in the polymerization.

It is known that the nitrogen and vinyl ether compounds can be removed from the impure N-vinylpyrrolidone product by distillation only at considerable expense. DE-A 37 36 603 (BASF) discloses a process in which the impurities are removed with an acidic ion exchanger. U.S. Pat. No. 5,329,021 (ISP) describes the purification of N-vinylpyrrolidone by multistage fractional crystallization.

However, the application of fractional crystallization as described in U.S. Pat. No. 5,329,021 has the disadvantage that the purifying action of each crystallization stage is relatively poor. In the U.S. patent, the vinylpyrrolidone to be purified is introduced into the first purification stage in which it is cooled to a temperature which is from about 1° C. to 5° C. below the melting point of the introduced stream, resulting in a crystalline N-vinylpyrrolidone phase and a liquid residue phase. The two phases are then separated from one another, the crystalline phase is heated to a temperature at which the crystals liquefy (the melt), and the melt is subjected to further crystallization steps. The disadvantage in this case is that the melt is supercooled in the crystallization, which results in uncontrolled crystal growth, which impairs the purifying action.

In addition, with the interconnection of the stripping stages described in U.S. Pat. No. 5,329,021 it is possible to obtain a particular yield only with increased expense for apparatus for the following reasons. The described process is based on the well-known countercurrent principle in which, after each crystallization stage, the crystals are separated from the crystallization residue, and the respective crystal streams are introduced into the stages with the next higher stage number, while the crystallization residue streams are introduced into the stages with the next lower stage number. In this case, the entering stream which is to be purified divides the stages into what are called purification stages and stripping stages. Since even multistage layer crystallization systems are normally operated with only one crystallization apparatus, buffer tanks are required between the individual crystallization stages. This means that the expense for the apparatus for the process increases with the number of separation stages required.

It is an object of the present invention to modify the process of fractional crystallization for purifying N-vinylpyrrolidone so as to achieve distinct advantages, compared with previously known processes, in respect of the expense of purification and thus the economics of the purification.

We have found that this object is achieved by applying an N-vinylpyrrolidone seed layer before the crystallization to the surfaces of the crystallizer from which crystals grow during the crystallization.

The invention thus relates to a process for purifying N-vinylpyrrolidone by crystallization in a crystallizer, where those surfaces of the crystallizer from which crystals grow during the crystallization are covered with an N-vinylpyrrolidone seed layer before the crystallization. Preferred embodiments of this process are defined in the dependent claims.

The crystallizer which is used according to the invention is not intrinsically subject to any particular restriction. Crystallizers which have proven particularly suitable are those whose function is based on the formation of crystals on cooled surfaces. DE 26 06 364, DE 17 69 123, EP 0 218 545, EP 0 323 377, CH 645 278, FR 266 89 46 and U.S. Pat. No. 3,597,164 describe suitable apparatus.

According to the invention, an N-vinylpyrrolidone seed layer is produced before the crystallization on those points or surfaces on which crystals are to form. The processes which are suitable according to the invention for producing the seed layer are not intrinsically subject to any restriction. It is possible according to the invention to use either an N-vinylpyrrolidone melt or an N-vinylpyrrolidone solution to produce the seed layer. Thus, if the term N-vinylpyrrolidone melt, or melt, is used hereinafter, this term applies equally to an N-vinylpyrrolidone solution, or solution. In is a preferred embodiment of the invention, this seed layer is produced by freezing an N-vinylpyrrolidone melt film wetting these points or surfaces. It is preferable for this purpose to bring about a supercooling on the crystallizer surfaces. In another preferred embodiment of the invention, this seed layer is produced by applying a two-phase layer of N-vinylpyrrolidone melt with suspended N-vinylpyrrolidone crystals to the crystallizer surfaces. This has the advantage that, unlike the freezing of the single phase liquid seed layer, less intense cooling is necessary, because the suspended crystals themselves act as crystallization nuclei. The cooling temperature in this case is preferably at the equilibrium temperature (melting point) of the suspension used.

The production of the two-phase suspension is not intrinsically subject to any restriction. In a preferred embodiment of the invention, crystals are frozen out of a melt of the mixture to be separated and are introduced into the melt. Crystals are preferably frozen out in what are called scratch coolers or stirred vessels, in particular with wall-sweeping stirrers, by in-direct cooling and are conveyed with the aid of scraping elements from the cooled walls into the suspension. It is also possible in addition to produce crystals directly in the melt or solution, by cooling the melt either via the crystallizer itself or via coolable elements (eg. cold fingers, cooling sections or stirred tanks) which are incorporated in the crystallizer or other apparatus, and to produce a suspension in this way. This has the advantage that the crystals do not have to be scraped off. The use of coolable elements is advantageous because it is unnecessary to cool the entire crystallizer. It is also possible to produce a suspension inside the crystallizer or outside it and to allow the crystals to sediment out of the suspension in the crystallizer onto the crystallization surfaces, where they act as seed crystals. The solids content of the suspension is from 0 g of solid/g of suspension to 60 g of solid/g of suspension.

In a preferred embodiment of the invention, the suspension is applied to the crystallizer surfaces by filling the crystallizer with the suspension and then emptying it. A layer of suspension remains on the crystallizer surfaces after the emptying and is then frozen on (at its equilibrium temperature). A corresponding process is possible when the suspension is produced in the crystallizer itself. There is also the possibility in addition to apply the suspension to the crystallizer surfaces via conventional distributor devices (eg. nozzle systems or plates). It is possible in this way to avoid filling the apparatus with subsequent emptying.

The seed material preferably used in both embodiments comprises the crystals leaving the particular crystallization stage. However, it is also possible in addition to use other N-vinylpyrrolidone of higher or lower purity, preferably higher purity. The crystallization is carried out after production of the seed layer.

The processes for carrying out the crystallization are not intrinsically subject to any special restriction and are known to the skilled worker. Suitable crystallization processes are described, for example, in U.S. Pat. No. 5,329,021, DE 26 06 364, DE 17 69 123 and EP 475 893. After application of the seed layer, according to the invention the vinylpyrrolidone to be purified is introduced as melt or solution into the first purification stage in which it is cooled to its equilibrium temperature (melting point), resulting in a crystalline N-vinylpyrrolidone phase and a liquid residue phase. The equilibrium temperature is from +14.4° to –6° C., depending on the composition of the N-vinylpyrrolidone to be separated. These two phases are separated from one another. The crystalline phase which has been removed is subsequently heated to a temperature at which the crystals liquefy (the melt), and this melt is subjected where appropriate to further crystallization steps. It is likewise possible to subject the residue phase to further crystallization steps as described in detail below.

The crystallization process according to the invention is carried out in one or more crystallization stages. The crystallization stages can generally be divided into purification stages and stripping stages. In each purification stage and stripping stage a crystallization is performed. In the purification stages the N-vinylpyrrolidone to be purified or purer crystals are employed. In the stripping stages the less pure crystallization residue is employed. The N-vinylpyrrolidone to be purified is introduced into the first purification stage and, after application of an N-vinylpyrrolidone seed layer, subjected to a crystallization. After the crystallization, the crystals are separated from the crystallization residue and introduced into the next purification stage, where the process is carried out likewise. The crystallization residue from the first purification stage is introduced into the stage with the next lower stage number, a stripping stage, and there subjected correspondingly to a crystallization. This process is based on the process of the countercurrent principle which has been described in the publications DE 26 06 364, DE 17 69 123, EP 475 893 and U.S. Pat. No. 5,329,021. This entails the crystal streams being introduced into the stages with the next higher stage number and the crystallization residue streams being introduced into the stages with the next lower stage number.

BRIEF DESCRIPTION OF THE DRAWINGS

FIG. 1 shows an example of a 5-stage crystallization system which can be used for carrying out the process according to the invention. In this, the stream (0) to be purified is passed into stage 4 (first purification stage) and subjected to a crystallization. The crystals (4.1) from stage 4 are introduced into the following stage 5 (second purification stage) and subjected to a crystallization. The crystals from stage 5 leave the latter as a stream (5.1) which represents the required purified N-vinylpyrrolidone. The crystallization residue from stage 4 is introduced as stream 4.2 into stripping stage 3. The crystallization residue from stage 5 (stream 5.2) is introduced into stage 4. The process corresponds in the other stages, ie. there are introduced into a stage the crystals from the preceding stage and the crystallization residue from the subsequent stage. In this case, the entry stream (0) divides the stages into purification stages 4 and 5 and stripping stages 1 to 3, which together correspond to crystallization stages 1 to 5. When carrying out the process according to the invention, an N-vinylpyrrolidone seed layer is applied to the crystallization surfaces before the crystallization in each crystallization stage.

Figure 1:
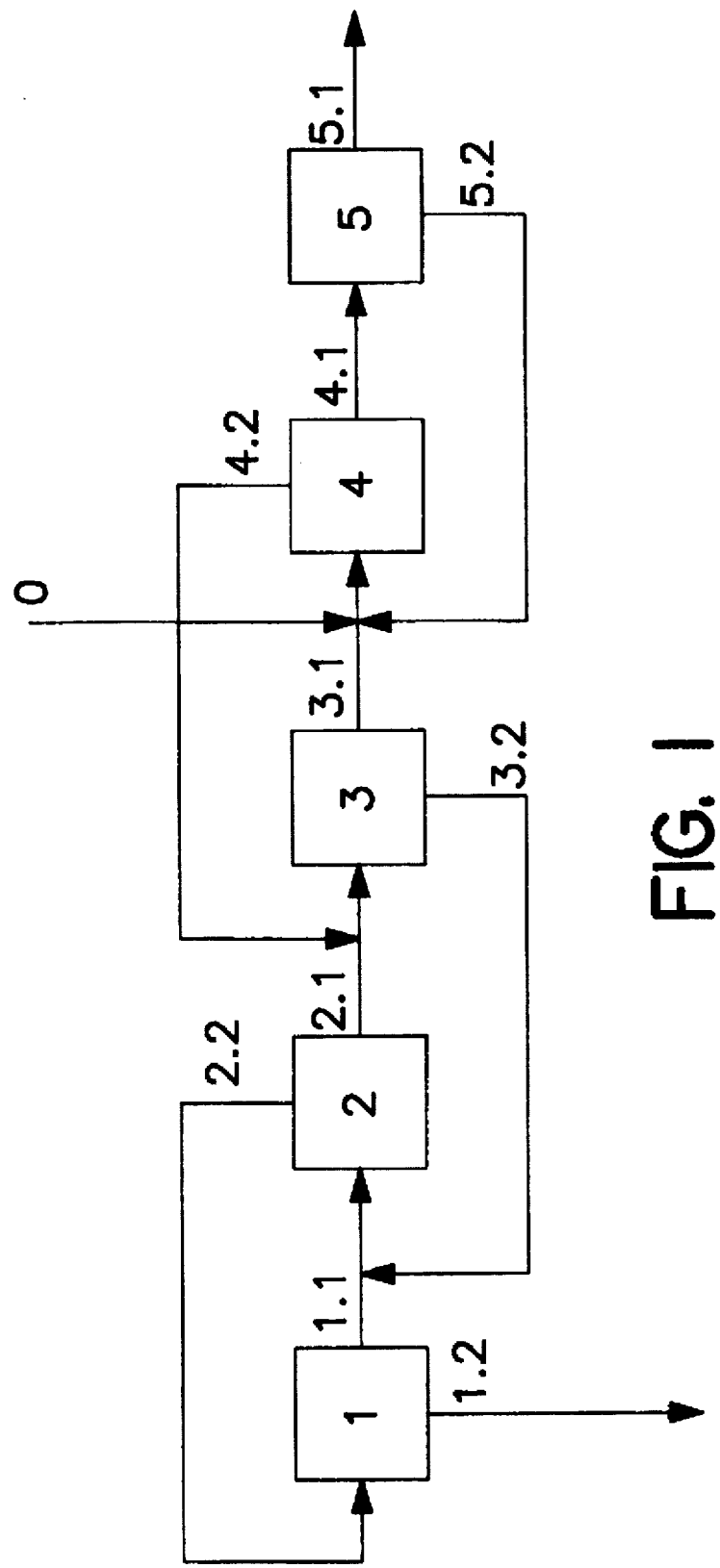
FIG. 1 is a diagrammatic representation of a crystallization system for carrying out the process.
Figure 2:
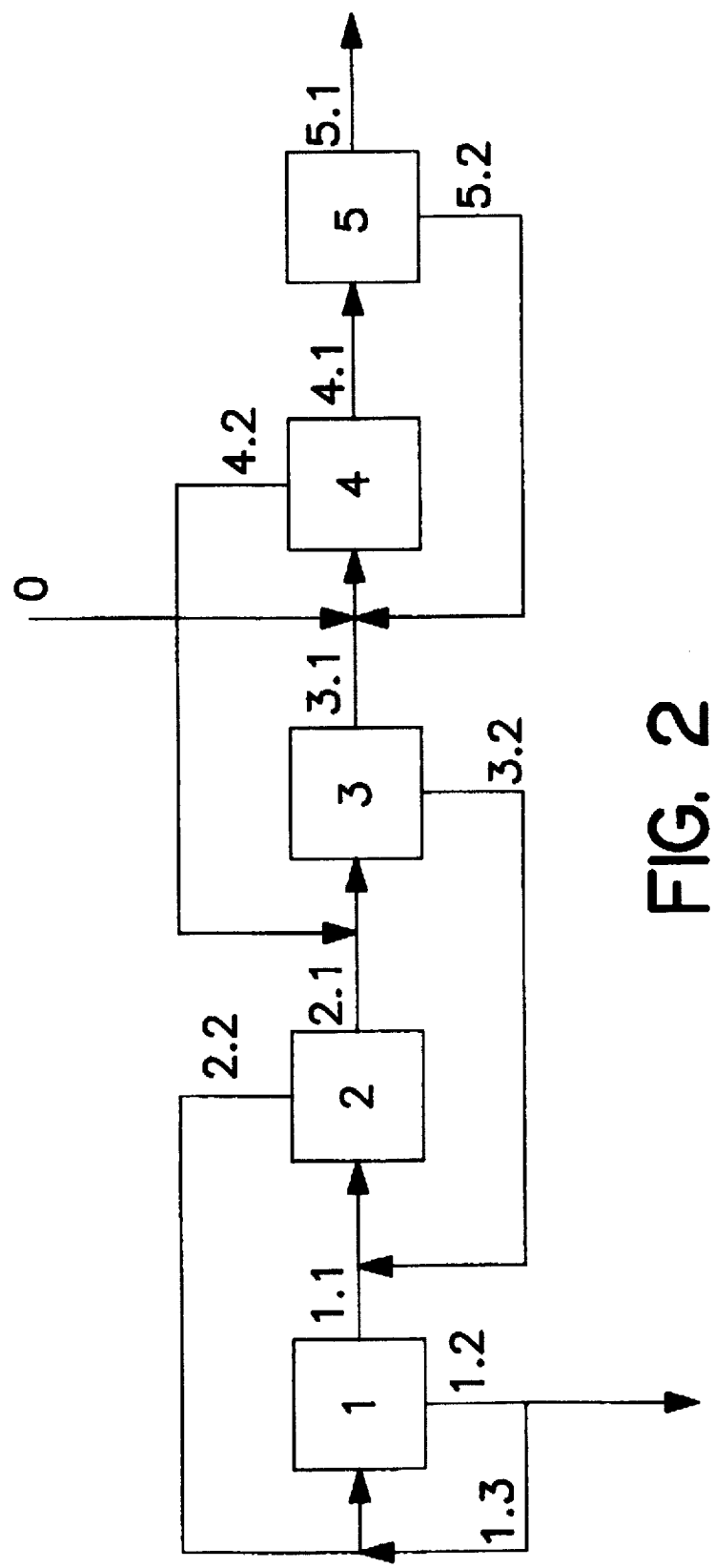
FIG. 2 sets forth a preferred embodiment of the system of FIG. 1.

In a preferred embodiment of the invention, the crystallization residue leaving the first crystallization stage is partly returned to this stage. A preferred embodiment of this type is illustrated in FIG. 2. In this, the same numbers as in FIG. 1 designate the same stages and streams. The crystallization residue (1.2) leaving the first crystallization stage (stripping stage 1) is partly returned to this stage as a stream (1.3). The ratio of stream (1.2) to stream (1.3) (return ratio) is from 0 to 1.0 depending on the objective.

The ratio of crystallization residue leaving the first crystallization stage to that which is returned (return ratio) is preferably from 0.1 to 0.95. The number of crystallization stages, and thus also of purification and stripping stages, depends on the object of the separation and can be established by the skilled person in conventional tests. The crystallization comprises at least one crystallization stage, including at least one purification stage, in any event. Two purification stages and one stripping stage are preferred.

The N-vinylpyrrolidone to be purified is not intrinsically subject to any restriction. It is possible according to the invention to use any desired N-vinylpyrrolidone. In particular, N-vinylpyrrolidone prepared by the vinylation of pyrrolidone with acetylene is used. This N-vinylpyrrolidone can be prepurified in a suitable manner, for example by distillation.

The process according to the invention can be carried out as dynamic or static process or as combination of these two processes. Static processes are preferably used in the stripping part of the system. In the static processes described, for example, in U.S. Pat. No. 3,597,164, EP 0 323 377 and FR 2 668 946, the liquid phase is agitated only by free convection (stationary melt), while in the dynamic processes the crystallization is carried out with forced convection of the liquid phase, ie. the melt is in flowing motion. This can take place by a forced flow in heat exchangers through which there is complete flow, as described, for example, in DE 26 06 364, or by applying a falling fill to a cooled wall, as described, for example, in DE-B 17 69 123 and EP-B 0 218 545.

After carrying out the process according to the invention it is possible to carry out additional purification steps. It is particularly suitable to wash the crystal layer, preferably with a purifying liquid, eg. the residual liquid (mother liquor) from the previous crystallization, as described in DE 37 08 709, and/or to carry out what is called sweating of the crystal layer. In sweating, the temperature of the crystal layer is raised, whereupon there is preferential melting of the more impure regions of the crystal layer and thus an additional purifying action is achieved.

The N-vinylpyrrolidone purified by the process according to the invention contains 99.5 to 99.999% by weight based on 100% by weight pure N-vinylpyrrolidone, or 5000 to 10 ppm impurities. This N-vinylpyrrolidone meets the requirements made in the foodstuff industry sector or in the drugs sector.

The invention is illustrated in detail by means of the following examples, which represent preferred embodiments of the invention.

EXAMPLE 1

N-Vinylpyrrolidone with an initial impurity of 0.6% by weight based on 100% by weight N-vinylpyrrolidone (this impurity concentration corresponds to the impurity concentration mentioned in U.S. Pat. No. 5,329,021) was crystallized in two purification stages and four stripping stages in a crystallizer as described in DE-A-26 06 364 (BASF). This entailed a two-phase suspension consisting of N-vinylpyrrolidone melt with suspended N-vinylpyrrolidone crystals being applied as seed layer to the surfaces of the crystallizer in all crystallization stages. To produce the seed layer, the crystallizer was filled with the melt to be purified in the particular stage, and a suspension was produced by cooling the apparatus. The apparatus was then emptied, and the suspension remaining on the crystallizer surfaces was frozen solid. The equilibrium temperatures of the melts during the crystallization in the individual stages were as follows:

Purification stage 5: 13.5° to 12.9° C.
Purification stage 6: 13.8° to 13.6° C.
Stripping stage 1: 13.1° to 12.6° C.
Stripping stage 2: 12.5° to 11.4° C.
Stripping stage 3: 11.2° to 8.5° C.
Stripping stage 4: 8.5° to 4.3° C.

Apart from stripping stage 4, which was carried out statically, all the other stages were carried out dynamically. The ratio of the crystal weight frozen out in one stage to the crystal weight employed in this stage was 0.8 in the first purification stage and 0.75 in the second purification stage. An impurity concentration of 0.102% by weight (based on 100% by weight N-vinylpyrrolidone) in the crystals was achieved in the first purification stage. This impurity concentration is a factor 4 lower than in the U.S. patent (where the impurity concentration was 0.4% by weight (based on 100% by weight N-vinylpyrrolidone)). The crystals are then introduced into a second purification stage and leave this with an impurity concentration of 190 ppm, which means that the impurity concentration is lower by a factor of about 2.5 than in the U.S. patent, where the impurity concentration was 500 ppm.

Thus, compared with known processes, the impurity concentration achieved in the purified N-vinylpyrrolidone with the process according to the invention, due to application of an N-vinylpyrrolidone seed layer before the particular crystallization, with identical starting conditions, same number of purification stages and identical weight of crystals frozen out based on the melt employed, is a factor of 2.5 lower. With the same product specification, this means a saving of purification stages and thus a considerable reduction in the expense necessary for separation.

EXAMPLE 2

This example shows that the expense for purification of N-vinylpyrrolidone can be additionally reduced by returning the crystallization residue emerging from the first crystallization stage, since this reduces the number of crystallization stages. An N-vinylpyrrolidone stream with 0.8% by weight impurity (based on 100% by weight N-vinylpyrrolidone) was subjected to a multistage crystallization, with a two-phase N-vinylpyrrolidone seed layer being applied to the crystallizer surfaces as in Example 1 in each crystallization stage in accordance with the process according to the invention. The number of crystallization stages corresponded to the total of the purification and stripping stages indicated in the table below. The equilibrium temperatures of the melt in the individual stages were as follows:

| | Stage | | | | |
|---|---|---|---|---|---|
| Return ratio | 1 (Stripping stage) | 2 (Stripping stage) | 3 (Stripping stage) | 4 (Purification stage) | 5 (Purification stage) |
| RF = 0 | 11.0 to 6.7 | 12.7 to 11.0 | 13.4 to 12.6 | 13.6 to 13.4 | 13.9 to 13.8 |
| RF = 0.6 | — | 12.0 to 7.1 | 13.3 to 12.3 | 13.6 to 13.4 | 13.9 to 13.8 |
| RF = 0.85 | — | — | 12.9 to 6.7 | 13.5 to 13.3 | 13.9 to 13.8 |

In all the examples, a crystal product stream with <100 ppm impurity was obtained in the second purification stage. The ratio of N-vinylpyrrolidone in the crystal product stream in the second purification stage to the N-vinylpyrrolidone used (in the first purification stage), ie. the yield, was at least 0.90. The ratio of the weight of crystals frozen out in one stage to the weight of crystals used in this stage was 0.65 for all cases under consideration and in all stages.

The following table shows that the number of stages can be reduced from 5 to 3 depending on the return ratio (return of the crystallization residue emerging from the first crystallization stage to this stage). In this case, the first crystallization stage corresponds to the first stripping stage.

TABLE

| Return ratio | RF = 0 | RF = 0.6 | RF = 0.85 |
|---|---|---|---|
| Number of stages | 5 | 4 | 3 |
| Number of purification stages | 2 | 2 | 2 |
| Number of stripping stages | 3 | 2 | 1 |
| Impurity concentration in the product [ppm] | 50 | 51 | 79 |
| Yield | 0.94 | 0.93 | 0.94 |

As is evident from the table, the number of stripping stages is reduced by the process according to the invention with a return ratio of 0.6 or 0.85, without losses of yield occurring or the resulting product not complying with specifications.

Hence the advantages which can be achieved with the process according to the invention are that the expense for apparatus and energy for the purification of N-vinylpyrrolidone can be considerably reduced. This applies to the number of stripping stages necessary for achieving a particular product specification and required yield and the purification stages in the process.

We claim:

1. A process for purifying N-vinylpyrrolidone by crystallization in a crystallizer, wherein those surfaces of the crystallizer from which crystals grow during the crystallization are covered with an N-vinylpyrrolidone seed layer before the crystallization.

2. The process as claimed in claim 1, wherein the seed layer is produced by freezing a molten film of N-vinylpyrrolidone.

3. The process as claimed in claim 1, wherein the seed layer is produced by applying a two-phase layer of N-vinylpyrrolidone melt or solution with suspended N-vinylpyrrolidone crystals.

4. The process of claim 1, wherein the crystallization is carried out in three crystallization stages, of which two are purification stages and one is a stripping stage.

5. The process as claimed in claim 4, wherein the crystals leaving the particular crystallization stage are used to produce the seed layer.

6. The process as claimed in claim 4, wherein the crystallization residue emerging from the first crystallization stage is partly returned to this crystallization stage.

7. The process of claim 6, wherein the ratio of emerging to returned crystallization residue is from 0 to 1.0.

8. The process of claim 6, wherein the ratio of emerging to returned crystallization residue is from 0.1 to 0.95.

* * * * *